United States Patent [19]

Ouaknine

[11] 4,196,519

[45] Apr. 8, 1980

[54] APPARATUS FOR RESETTING A DENTAL PROSTHESIS

[76] Inventor: Gilbert Ouaknine, 6, rue Mazzini, 11100 Narbonne, France

[21] Appl. No.: 883,898

[22] Filed: Mar. 6, 1978

[30] Foreign Application Priority Data

Jan. 3, 1977 [FR] France ............................. 77 06545
Sep. 9, 1977 [FR] France ............................. 77 27554

[51] Int. Cl.² ............................................. A61C 9/00
[52] U.S. Cl. ........................................ 433/49; 433/56
[58] Field of Search ........................... 32/32, 40 R, 17

[56] References Cited

U.S. PATENT DOCUMENTS

| 1,986,628 | 1/1935 | Edwards | 32/32 |
| 2,670,538 | 3/1954 | Thompson | 32/32 |

Primary Examiner—Robert Peshock
Attorney, Agent, or Firm—Shlesinger, Arkwright, Garvey & Dinsmore

[57] ABSTRACT

An apparatus for resetting of a dental prosthesis comprising a bottom plate having means for fixing the bottom plate to a support plate, at least two pressure columns fastened to said bottom plate and provided at their upper ends with a connecting cross piece, a movable element connected to the connecting cross piece and adapted to be moved parallel to the pressure columns, means for moving the movable element, a pressure element articulatably connected to the movable element so as to provide a clearance therebetween while permitting relative rotation and adapted to be able to exert pressure on the prosthesis mounted on the support plate, and adjustable stop means for adjustably limiting the travel of the pressure element toward the support plate and the prosthesis mounted thereon.

17 Claims, 5 Drawing Figures

APPARATUS FOR RESETTING A DENTAL PROSTHESIS

The invention relates to a device for resetting of a dental prosthesis. The object of resetting of the dental prosthesis worn by a partially or completely toothless person is to eliminate the play which appears a certain time after the original setting in place of the prosthesis, between the base of the prosthesis and the gum or the mucous membrane of the patient. This play comes from a settling of the gum, essentially due to the pressure of the prosthesis, which is of rigid material in contact with the gum, and to the resorptions which are produced as a result of the dental extractions during healing. The operation of resetting tends to put a supplementary thickness of material in place on the base of the prosthesis in such a manner as to perfectly fill the free space which has appeared between the prosthesis and the gum.

Some practicioners do the resetting directly in the mouth, but the disadvantages of this practice, i.e. poor quality, burrs, presence of bubbles in the material, risk of burning the mucous during polymerisation of the resin, etc., have forced most professionals to prefer the process hereinafter described.

A plaster impression is arranged on the base of the prosthesis, the prosthesis is placed in the mouth and applied against the gum of the patient to force the excess plaster into occlusion position. Thus, after hardening of the plaster, a model is obtained which is provided with ideal excess thickness to be realized to take up the aforementioned play. The prosthesis with its excess thickness is then sent to the laboratory and the prosthesist makes a plaster mold of a negative impression of the base of the prosthesis with its excess thickness. After hardening of the plaster and removal of the prosthesis, this cast then furnishes a reproduction of the actual form of the gum of the patient. The plaster arranged on the base of the prosthesis is then removed and a pasty layer of resin of the same nature as that of the prosthesis is put in its place. The prosthesis and its resin layer are placed on the plaster maxillary impression and the excess of resin is packed by manual pressure. After hardening by baking of the resin, for instance by autopolymerisation, the prosthesis is lifted from the plaster impression, then submitted to finishing operations, such as rough grinding, polishing.

The above described process is today carried out without precise apparatus and is accompanied by many inconveniences. The most serious resides in the fact that it is impossible to apply the prosthesis and its layer of resin on the plaster maxillary impression by manual pressure exerted by an operator, into a position which precisely corresponds to the occlusion position of the mouth. In effect, the prosthesist has no objective means to judge at what precise moment the prosthesis is exactly in place on the impression, to cease exertion of the pressure. The excess thickness needed to fill the space between the prosthesis and the gum can be too fine because of too great pressure or too thick because of too little pressure. In both cases, the patient is still not in ideal occlusion position between top maxillary and bottom maxillary. It is also to be noted that the pressure exerted by the prosthesist is not totally uniform and can lead to local imperfections of the prosthesis, giving it an incorrect position in the mouth.

Another fault can be generated by an accidental displacement either in the anteroposterior direction or in the transverse direction, when the prosthesis is placed on the plaster maxillary impression. There again, the position of occlusion in the mouth will be deficient.

The resetting process described is awkward, requires sustained attention on the part of the operator and requires rather long manipulation time. Particularly at the time of casting of the plaster maxillary impression, a plaster foundation must be cast and fitted to support this impression. Moreover, in case the prosthesis is baked, it is necessary to use a clip to hold it on the maxillary impression during the baking.

The present invention is proposed to furnish a device which can effect a rapid and precise resetting of a prosthesis.

One object of the invention is particularly to permit precise adjustment of the excess thickness of resin arranged on the base of the prosthesis, so as to guarantee a correct position of occlusion in the mouth.

Another object of the invention is to avoid displacement in anteroposterior direction or in transverse direction.

Another object is to render the resetting process of easy and rapid execution and to delete certain manipulations which result in losses of time.

For this, the device as in the present invention includes a bottom plate provided with means for fixation and positioning of a support plate, at least two pressure columns fastened to said plate and integral at their tops with a connecting crosspiece, a movable element connected to this connecting crosspiece and adapted to be moved parallel to the columns, maneuvering means for this movable element, a pressure element upon said movable element and adapted to be able to apply pressure on the prosthesis, which is to be mounted on the support plate, and finally adjustable stop means, designed to adjustably limit the course of the pressure element toward the support plate and its prosthesis thereon.

As will be more clearly understood hereinafter, this constantly facilitates the operations of resetting and permits the exercise of suitable pressure on the prosthesis with its resin layer, permitting its application on the maxillary impression in a position which precisely corresponds to the occlusion position of the mouth.

According to a preferred embodiment, the device is completed by a base provided with fixation means for the bottom plate in order to stabilize it during use or to allow its withdrawal. The prosthesist thus works in excellent working conditions; for the baking of the resin, the plate can be withdrawn from its base and the device to the exclusion of the base can be arranged in a drying oven. The prosthesis is held against the plaster impression during the entire baking by clamping between the pressure element and the bottom plate.

Also, the device of the invention can include at least two positioning assemblies for the prosthesis, carried by the bottom plate and situated at the periphery of the support plate. These assemblies each include a movable contact element for contact against the prosthesis, particularly a shaft which is oriented towards the prosthesis, and they are each designed to permit definition of a precise position of the prosthesis in transverse and anteroposterior position, with the aid of these elements.

The invention will be better understood in the following detailed description relative to the attached drawings, showing one nonlimiting embodiment.

Figure 1:
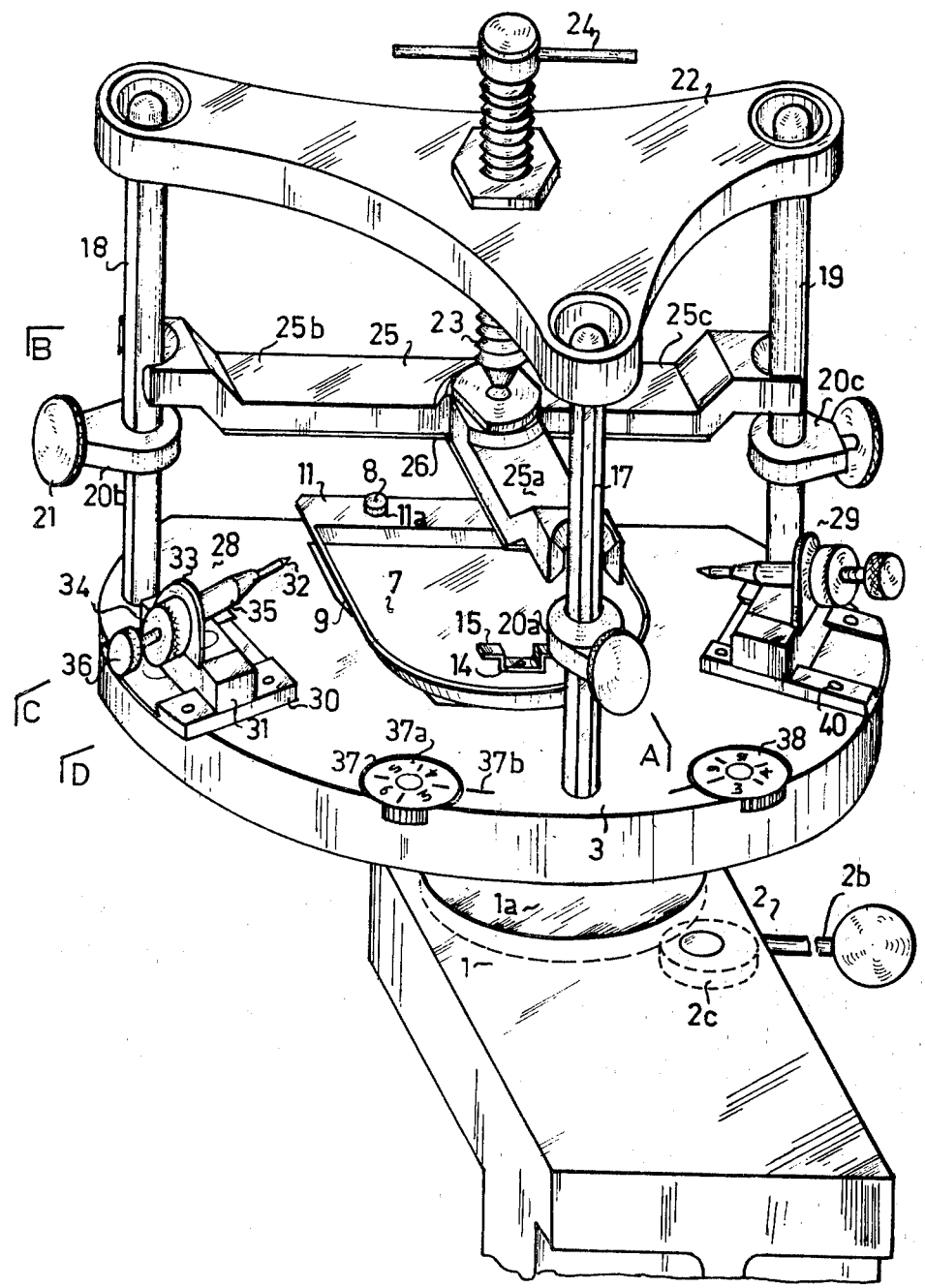
FIG. 1 is a partial perspective view of a device according to the invention.

The device includes a base 1 provided with a circular recess 1a and blocking means 2 to assure blocking of a plate 3 in relation to this base.

Plate 3 is blocked on base 1 by a circular projection on its bottom face which is lodged in the circular recess 1a of the base. This arrangement confers less bulk on the base.

Also blocking means 2 are constituted of a eccentric 2c, which is maneuverable by means of a lever 2b to be able to press against the circular projection of plate 3. These means are very practically implemented.

The base is also provided at the bottom with a bit and tightening means which are not shown, adapted to allow attachment to the edge of a table or the like.

Plate 3 has fixation and positioning means for a support plate 7 on its top surface. These means are constituted of hollow or relief centering structures such as two pins 8 arranged in projection on them, and also of magnetic means such as a small magnetic plate 9 glued onto this plate.

Support plate 7 is constituted of a ferromagnetic metal cupel, for example a swaged steel cupel, which has a border 11 at its posterior, provided with two openings 11a, which cooperate with pins 8 of the plate. The support plate can thus be very rapidly put in place on plate 3 in a precise position, always identical, or withdrawn from this position almost instantaneously.

Support plate 7 is intended to facilitate the casting and to support a plaster impression on which the prosthesis to be reset will be mounted. A screw 14 passes through the support plate and is screwed onto a tab 15 with raised wings, which is situated to the side of the impression and is to be immersed in it at the time of its casting, while an opening is provided in the small magnetic plate 9 for a lodging for the head of screw 14. Thus, the maxillary impression can be perfectly mounted on the support plate and can if desired be withdrawn and rapidly returned to its place.

Also, plate 3 has three pressing columns 17, 18 and 19, arranged in a triangle and sufficiently removed from one another that the support plate can pass through and be lodged between them.

On each column is mounted a sliding stop 20, provided with a blocking element such as set screws 21, to fix the column in adjustable position.

At their tops, columns 17, 18 and 19 are united by a connecting crosspiece 22 to which they are fastened. Maneuver means such as a small lever 24 are for turning this screw.

A pressure element 25 is connected to the bottom of screw 23 by an articulation 27 which gives this element a certain clearance during rotation in relation to said screw.

Element 25 includes three arms 25a, 25b, and 25c, of which the ends are designed to form a triangle to come into contact with the prosthesis 13. Element 25 is articulated on screw 23 which carries it, approximately at the level of the center of gravity of this contact triangle. It is thus capable of being applied correctly to three points of the prosthesis, one anterior axial point and two posterior lateral points, and it can thus exert an equal pressure on it.

Figure 2:
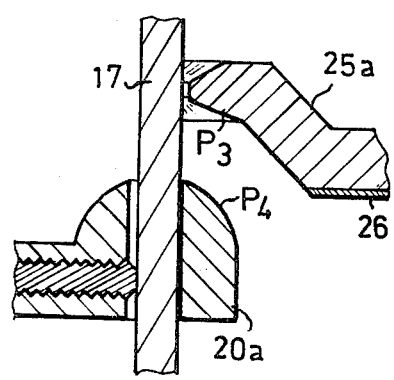
FIGS. 2 and 3 are details respectively in cross section A and B.

Pressure element 25 can be in the form of a T, as shown in FIGS. 1 and 2, or it can of course be in other forms, such as Y, K, etc. The ends of the three arms 25a, 25b and 25c of this pressure element are provided with notches which fit the form of the columns with some clearance and assure a guiding of the element in the course of its movements.

Figure 3:
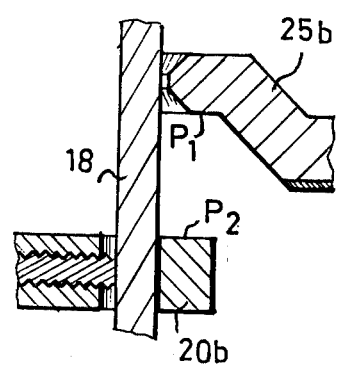

The ends of the two lateral arms 25b and 25c, in FIGS. 1 and 3, have flat bottom surfaces $P_1$, to come in contact with the flat surfaces $P_2$ of the corresponding sliding rings 20b and 20c. On the contrary, sliding rings 20a, in FIGS. 1 and 2, corresponding to the central arm, has a convex surface $P_4$, which is essentially part of a sphere, against which is contacted a fitted conical surface $P_3$, provided at the end of central arm 25a. Tests have shown that the combination of the two lateral contacts with flat surfaces and the central contact with spheroconical surface confers a precise position on the pressure element, unique for each configuration, which is precisely reproducible in the second work phase by the prosthesist.

Pressure elements 25 is provided on its bottom surface which comes in contact with the prosthesis with a thin coating 26 of a semi-rigid synthetic material, which deletes the risk of the prosthesis being damaged upon contact.

Figure 4:
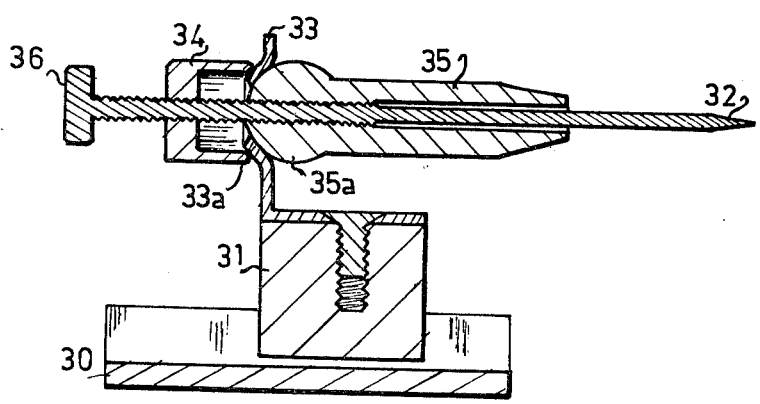
FIGS. 4 and 5 are details respectively in cross section C and D.
Figure 5:
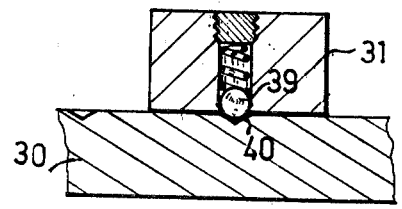

Besides, two positioning assemblies 28 and 29 are provided at the periphery of support plate 7, shown in detail in cross section in FIGS. 4 and 5. These assemblies are arranged symmetrically in relation to the axial plane of the resetting device and are each oriented at an angle of approximately 60° in relation to this axial plane.

Each positioning assembly includes a track 30 which is integral with bottom plate 3, a slide 31 which can slide on this track along a radial direction in relation to this plate, and a contact element with a movable shaft 32 with a pointed end, a support 33 of this contact element, integral with the slide and able to confer mobility on this element, bringing it into contact against the prosthesis, and finally blocking means 34 of this contact element.

In the preferred embodiment shown in the drawings, movable shaft 32 is threaded on a portion of its length and screwed in a guide sleeve 35, provided for this with a threaded passage. This sleeve has a spherical outside surface 35a which fits the form of a surface 33a on support 33. Blocking means 34 are constituted of a collar nut, screwed on shaft 32 to block it by pressure on support 33 between sleeve 35 and said nut 34.

Thus, movable shaft 32, mounted on a swivel joint, can pivot in a predetermined sector and can be moved longitudinally in relation to its axis toward the prosthesis by screwing. The combination of these movements puts its end in contact against a given point of the prosthesis. It is to be noted that shaft 32 is provided at the rear with a milled head 36 to facilitate its screwing.

The track and the slide, which can have any suitable form, particularly but not exclusively a dovetail form, as shown, are associated to pawl and rachet means which permit definition of several predetermined discrete positions of this slide along the track. For example, these means can be constituted of a pair of ball bearings 39 mounted on springs on each side of the slide and capable of catching in several series of recesses 40 which are in the track.

Each positioning assembly can be associated with a position indicator 37 or 38 which is situated nearby and which permits marking at what point on the prosthesis the contact of the movable element is effected.

For example, each indicator 37 or 38 includes a revolving wheel 37a, on the plate, on which are marked the numbers of the teeth of the prosthesis which are to be situated opposite the positioning assembly, as in teeth 3-4-5-6, in the example. An index 37b is provided on the plate to designate the interdentary space at the level of which the contact of the movable element is effected.

For better understanding of the function of each element of the device and the advantages, it will be explained hereinafter in the development of a resetting operation.

The prosthesist receives the prosthesis from the dentist provided with a hardened plaster which represents the ideal excess thickness of resin to set in place. This plaster has been cast to the required form in the mouth of the patient in such a manner as to fill the existing play between the gum and the prosthesis.

First, the prosthesist casts a plaster negative impression of the prosthesis with paste. The semi-liquid plaster is mounted on the support plate 7 and the prosthesis is applied and pressed onto it.

When the plaster of the impression is dry, the prosthesist places the support plate assembly, impression and prosthesis on plate 3 of the device. The support is maintained by magnetization and is perfectly positioned by the centering pins. The sliding stops 20 are in bottom position, and the screw 23 is lowered until pressure element 25 comes into contact by its three arms against the prosthesis. The articulation allows this element to make contact even if the prosthesis is in an inclined position.

The sliding stops are then raised along the columns to come in contact against the end of the corresponding arms. In this position, they are affixed on the columns by means of their set screws 21. Thus in place, they help to define the position of pressure element 25, the position which it will have to reproduce in the subsequent phase.

In order that the positioning of the prosthesis may be reproduced very precisely, the prosthesist uses assemblies 28 and 29. The slide is arranged on the track by pawl and ratchet effect, in a position as a function of the form of the prosthesis, shaft 32 is released and put in contact with a predetermined interdentary space of the prosthesis. The shaft is then blocked, the interdentary space is marked on indicator 27 or 28, and the slide is withdrawn by exerting a slight force on it to disengage the ball bearings from their notches.

When these operations are finished for the two positioning assemblies, the pressure element can be raised and the prosthesis removed by a traction on the support plate.

The maxillary impression is then lifted from the prosthesis. The hardened paste situated in the base of the prosthesis is removed. Once this is perfectly cleaned, a layer of pasty resin, before polymerisation, is arranged in the place of the aforementioned plaster.

The prosthesis which is thus prepared is again mounted on the maxillary impression and the assembly is again mounted on plate 3 of the device. The prosthesist again finds the position of the prosthesis by replacing the slide of each assembly 37 or 38 in its former position, and catching the ball bearings in the same notches. The ends of the shafts of the two assemblies then come in contact against the prosthesis and eliminate its displacement in transverse and anteroposterior direction.

The pressure element is lowered to abut against sliding stops 20, which stop it. At this moment, the excess resin has been forced out and the excess thickness 26 which remains on the prosthesis is very precisely identical to the excess thickness of hardened paste which is to be reproduced. No transverse or anteroposterior displacement is permitted because of the presence of shafts 32.

The device allows the prosthesis to be put under a press, without the base, in a drying oven. It suffices to unscrew the eccentric 2c from the base to free the press.

Once the resin is hardened, the pressure element is unscrewed and the prosthesis can be lifted from the impression.

Such a device considerably facilitates the resetting operations and permits their execution with great precision.

Of course, the invention is not limited to the terms of the preceding description, but includes all variations. The number of arms and the form of the pressure element can also differ.

I claim:

1. A device for resetting of a dental prosthesis comprising a bottom plate having fixation and positioning means for a support plate, at least two pressure columns fastened to said bottom plate and provided at their upper ends with a connecting crosspiece, a movable element connected to said connecting crosspiece and adapted to be moved parallel to the columns, a pressure element articulatably connected to said movable element so as to provide clearance therebetween while permitting relative rotation and adapted to be able to exert pressure on the prosthesis mounted on the support plate, and adjustable stop means for adjustably limiting the travel of the pressure element toward the support plate.

2. Device as in claim 1, wherein said movable element includes a screw in a threaded hole in the connecting crosspiece whereby rotation of said screw displaces said pressure element.

3. Device as in claim 2, wherein the pressure element includes three arms in a T-shaped configuration, the ends of said arms having a contact triangle which which contacts the prosthesis, and said pressure element being articulated on the movable element approximately at the level of the center of gravity of this contact triangle.

4. Device as in one of the claims 1, 2, or 4, wherein said stop means is adjustable for limiting the travel of the pressure element and comprises sliding stops mounted on the pressure columns, each stop being provided with a blocking element to fix its position on its column, and said pressure element being adapted to come into contact with said stops in the course of its displacement.

5. Device as in claim 4, and including three pressure columns arranged in a triangle, near which are situated the ends of said arms of the pressure element, whereby the ends of said arms may contact the sliding stops mounted on said columns.

6. Device as in claim 1, wherein the fixation and positioning means of the support plate on the bottom plate include magnetic means cooperatable with the support plate of ferromagnetic metal, and center structures in hollow or in relief which cooperate with matching structures on the support plate.

7. Device as in claim 1 including a base which is provided with fixation means for the bottom plate, for stabilizing said bottom plate during use or allowing its removal.

8. Device as in claim 7, wherein said base is provided with a bit and tightening means on the bottom to permit attachment to the edge of a table or the like.

9. Device as in claim 1 and including at least two prosthesis positioning assemblies mounted on said bottom plate and at the periphery of the support plate, said assemblies each including a movable contact element to contact the prosthesis and being adapted to permit definition by said elements of precise position of the prosthesis in transverse and anteroposterior relationship.

10. Device as in claim 9, wherein each positioning assembly includes a track integral with the bottom plate, a slide slidable on said track in a radial direction in relation to the plate, a support for the aforementioned contact element which is integral with the slide and can confer a mobility on the slide which allows it to be brought into contact with the prosthesis, and finally blocking means for the contact element.

11. Device as in claim 10, wherein the movable element of each positioning assembly includes a shaft oriented in the direction of the prosthesis to be able to be placed in contact against the prosthesis by its end, and mounted on a swivel joint to allow it to pivot within a predetermined sector, and said shaft being longitudinally mobile in relation to its axis.

12. Device as in claim 11, wherein the movable shaft is threaded on at least one portion of its length and is screwed in a guide sleeve which has a threaded passage, said guide sleeve having an external spherical surface which fits with the form of a matching surface provided on said support, and a blocking nut screwed on the shaft to block said shaft by pressure on the support between the guide sleeve and said blocking nut.

13. Device as in claim 12, and including pawl and ratchet means associated with the track and the slide to define a plurality of predetermined discrete positions of the slide along the track.

14. Device as in claim 10, wherein each positioning assembly is associated with a position indicator, marking at what level the contact of the movable element is effected on the prosthesis.

15. Device as in claim 14, wherein at least one sliding stop has a top surface of convex form, and the pressure element is provided on the column corresponding to said stop with a notch so that it will be guided by said column and with a conical surface adapted to that of the sliding stop for its contact with said stop.

16. Device as in claim 5, wherein the end of the central arm has a conical surface in contact with the convex surface of the corresponding sliding ring, and the two lateral arms have flat surfaces in contact with the flat surfaces of the corresponding sliding ring.

17. Device as in claim 1, wherein the pressure element is provided on its bottom surface which is to come into contact with the prosthesis with a thin coating of a semirigid material.

* * * * *